United States Patent
Molteno

(10) Patent No.: US 7,776,002 B2
(45) Date of Patent: Aug. 17, 2010

(54) OPHTHALMIC IMPLANT FOR TREATING GLAUCOMA

(75) Inventor: Anthony Christopher Bernard Molteno, Dunedin (NZ)

(73) Assignee: Molteno Ophthalmic Ltd., Dunedin (NZ)

( * ) Notice: Subject to any disclaimer, the term of this patent is extended or adjusted under 35 U.S.C. 154(b) by 723 days.

(21) Appl. No.: 10/594,381

(22) PCT Filed: Mar. 24, 2005

(86) PCT No.: PCT/NZ2005/000054

§ 371 (c)(1), (2), (4) Date: Jun. 11, 2007

(87) PCT Pub. No.: WO2005/092260

PCT Pub. Date: Oct. 6, 2005

(65) Prior Publication Data

US 2007/0249984 A1  Oct. 25, 2007

(30) Foreign Application Priority Data

Mar. 26, 2004 (NZ) .................................. 531977

(51) Int. Cl.
*A61M 1/36* (2006.01)
(52) U.S. Cl. ................. 604/8; 604/9; 604/264
(58) Field of Classification Search ............ 604/8, 604/9, 264
See application file for complete search history.

(56) References Cited

U.S. PATENT DOCUMENTS

| | | | |
|---|---|---|---|
| 4,457,757 A | 7/1984 | Molteno | |
| 4,750,901 A * | 6/1988 | Molteno | 604/8 |
| 5,178,604 A | 1/1993 | Baerveldt | |
| 5,300,020 A | 4/1994 | L'Esperance, Jr. | |
| 5,338,291 A * | 8/1994 | Speckman et al. | 604/9 |
| 5,370,607 A | 12/1994 | Memmen | |
| 5,397,300 A | 3/1995 | Baerveldt | |
| 5,454,796 A | 10/1995 | Krupin | |
| 5,476,445 A | 12/1995 | Baerveldt | |
| 5,558,629 A | 9/1996 | Baerveldt | |
| 5,616,118 A | 4/1997 | Ahmed | |
| 5,681,275 A | 10/1997 | Ahmed | |
| 5,785,674 A | 7/1998 | Mateen | |
| 5,868,697 A | 2/1999 | Richter | |
| 6,186,974 B1 | 2/2001 | Allan | |
| 6,261,256 B1 | 7/2001 | Ahmed | |
| 6,468,283 B1 | 10/2002 | Richter | |
| 6,589,203 B1 | 7/2003 | Mitrev | |

FOREIGN PATENT DOCUMENTS

NZ         215409        3/1986

* cited by examiner

*Primary Examiner*—Leslie R Deak
(74) *Attorney, Agent, or Firm*—Senniger Powers LLP

(57) ABSTRACT

An ophthalmic implant for treating or alleviating the symptoms of glaucoma having a plate shaped to fit the surface of an eye. The plate has an inner ridge that defines a primary drainage region. Intraocular pressure is reduced by the transfer of aqueous fluid from the interior of the eyeball through a tube to the primary drainage region. To minimize post-operative hypotony, a secondary drainage region is provided on the plate outside the primary drainage region and defined either by the outer edge of the plate or an outer ridge having a lower profile than the inner ridge. When the pressure of fluid in the primary drainage region builds, fluid spills into the secondary drainage region. Fluid that is transferred to the plate is absorbed in surrounding tissues.

19 Claims, 4 Drawing Sheets

OPHTHALMIC IMPLANT FOR TREATING GLAUCOMA

TECHNICAL FIELD

This invention relates to an ophthalmic implant for treating, preventing, and/or alleviating the effects of glaucoma. In particular, the invention relates to a glaucoma implant that reduces intraocular pressure, and maintains intraocular pressure at normal levels, while preventing undesirable excessive intraocular pressure reduction immediately following surgical implantation (post-operative hypotony).

BACKGROUND

Glaucoma is a term which refers to a group of eye diseases that gradually destroy vision. Vision loss due to glaucoma is caused by damage to the optic nerve. High intraocular pressure (IOP) is a risk factor for glaucoma. Glaucoma can also result in high IOP. Glaucoma implants therefore seek to reduce IOP within the eye and to maintain long-term IOP at normal levels.

The glaucoma implant of this invention is a further development and improvement on glaucoma implants invented by the same inventor which have been the subject of earlier patents.

U.S. Pat. No. 4,457,757 describes an implant that is inserted into an eye under the outer tissue layer (Tenon's tissue). The implant comprises a plate which is attached to the surface of the eyeball, and a tube that extends from the plate and is inserted into an anterior chamber of the eye. This enables aqueous fluid to be transferred, via the tube, from the anterior chamber to the plate where the fluid is absorbed into the surrounding tissue. IOP is thereby reduced.

One problem associated with implants of this kind is an excessive lowering of IOP following implantation (post-operative hypotony). This can cause damage to the eye resulting in impairment of vision.

U.S. Pat. No. 4,750,901 describes an improved implant that seeks to prevent post-operative hypotony. This implant has two elevated ridges on the upper surface of the plate. One ridge runs around the edge, or near to the edge, of the plate to help define and maintain a bleb into which fluid from the eye can drain and be absorbed into the overlaying Tenon's tissue. A subsidiary ridge defines a second smaller region within the area of the plate defined by the peripheral edge. During implantation, Tenon's tissue is drawn forward and stretched to cover the subsidiary ridge of the plate of the implant and sutured firmly to the sclera just in front of the plate. This creates a chamber into which fluid from the anterior chamber of the eye is drained. The tension that the tissue exerts on the subsidiary ridge enables fluid to escape on to the plate beyond the subsidiary ridge only when the pressure reaches a certain level. This reduces the possibility of fluid from the eye being too readily absorbed into the Tenon's tissue overlaying the plate in the initial few days after surgery and leading to undesirable excessive IOP reduction.

The plate of the implant described in U.S. Pat. No. 4,750,901 may be linked to one or more other plates with interconnecting tubes to allow passage of fluid from the first (primary) plate to subsidiary plates. This provides a greater surface area for more efficient dispersion of large amounts of aqueous fluid. However, the implantation of more than one plate and tube arrangement greatly increases the complexity and difficulty of surgical implantation. The subsidiary ridge principle described in U.S. Pat. No. 4,750,901 can be applied to any subsidiary plate.

Other glaucoma implants are also known, but these all have problems or disadvantages.

U.S. Pay. No. 5,178,604 (Baerveldt) describes an implant made from a soft elastomeric material for the purpose of avoiding trauma to the eye that can occur with an implant made from a rigid material. However, no such trauma or irritation has ever been observed by the inventor for the present application. Baerveldt claims that a softer material is easier to insert into Tenon's capsule. However, U.S. Pat. No. 6,261,256 (Ahmed) indicates that the opposite may in fact be the case.

U.S. Pat. No. 5,300,020 (L'Esperance, Jr.) describes an implant that is a stud designed to keep a channel open for drainage of aqueous fluid from the eye. However, this implant ignores the need for a plate to be attached to the tubular channel to prevent fibrous tissue capping the end of the channel and preventing the escape of fluid.

U.S. Pat. No. 5,370,607 (Memmen) describes a flexible band and reservoir/tube design with baffles on the surface of the reservoir to direct the flow of fluid.

U.S. Pat. No. 5,397,300 (Baerveldt) describes the use of one or more holes in the plate of the implant described in U.S. Pat. No. 5,178,604. The purpose of the holes is to provide tethering by fibrous tissue designed to stop the bleb distending too much and interfering with the action of the eye muscles and causing double vision (diplopia).

U.S. Pat. No. 5,454,796 (Krupin) describes an implant comprising a tube and a valve within the tube. However, as with all valve designs, there is a risk of blockage by blood clot or debris commonly occurring in the fluid of glaucomatous eyes.

U.S. Pat. No. 5,476,445. (Baerveldt) describes a temporary flow restricting seal beneath the plate of an implant. The implant is designed to provide a temporary, non-valved, flow-restricting device aimed at eliminating post-operative hypotony. The walls of the implant form a seal underneath the plate, between the plate and the sclera, into which the fluid drains. The fluid cannot escape until the pressure within the eye builds up beyond what can be sustained by the sutures holding the plate down onto the sclera The sutures are non-permanent and dissolvable. They anchor the plate to the sclera in the immediate post-operative period thereby preventing post-operative hypotony. The sutures then dissolve such that the plate is anchored only by the downward pressure of Tenon's tissue. This reduces the pressure required to effect fluid release from the anterior chamber. However, the placement of these sutures requires considerable additional surgical time. There is also the danger of fibrous tissue in-growth into the cavity nearest the point where the tube enters from the eye.

U.S. Pat. No. 5,558,629 (Baerveldt) describes an implant similar to the implant of U.S. Pat. No. 5,178,604, as well as additional features including a radio-opaque plate, the use of an absorbable ligature around the tube of the implant, the use of an absorbable plug to restrict the escape of aqueous fluid in the immediate post-operative period, the use of double lumen tubing, and the use of two parallel tubes. This implant would suffer from the same problems experienced by the implant of U.S. Pat. No. 5,476,445 discussed above.

U.S. Pat. No. 5,616,118 (Ahmed) describes an implant having a membrane valve system. The valve opens and closes depending on the intraocular pressure. Like all valved systems it carries the risk of blockage by blood colt or fibrin which would necessitate further surgery or removal of the implant. U.S. Pat. No. 5,681,275 (Ahmed) describes a double plate version and U.S. Pat. No. 5,785,674 (Ahmed) describes a winged version intended to stop strabismus (squinting).

U.S. Pat. No. 6,261,256 (Ahmed) describes an implant having ridges on the surface of the plate to stop it rolling up during insertion. However, in practise, creating multiple blebs by holes in the ridges to provide anchorage for fibrous tissue will tend to reduce the effectiveness of the device and result in higher long term intraocular pressures.

U.S. Pat. No. 6,468,283 (Richter) describes an implant of the stud design. The implant has a small disk at the outer end with a ridge intended to prevent blockage by fibrous tissue. In practise this disk is too small in the vast majority of cases and a cap of fibrous tissue will form over the disk preventing the drainage of fluid.

There is, therefore, a need for further improved implants. In particular, there is demand for a greater drainage area on a single plate to allow for efficient aqueous dispersion while minimising the complexity of surgical implantation. In addition, a lower profile implant is desirable to further assist insertion of the implant into Tenon's capsule. There is also a demand for improved contact between the subsidiary ridge and the overlying Tenon's tissue in order to raise the pressure at which fluid lifts the tissue off the subsidiary ridge and drains onto the larger area of the plate. This would improve the ability of the implant to prevent post-operative hypotony.

It is therefore an object of this invention to provide an implant for alleviating problems associated with glaucoma which avoids to at least some extent the problems associated with known implants, or to at least provide a useful alternative to known implants.

STATEMENTS OF INVENTION

In one aspect of the invention, there is provided an ophthalmic implant for treating or alleviating the symptoms of glaucoma, the implant having:
a) a plate shaped to fit the surface of an eye when implanted,
b) an inner ridge located on the upper surface of the plate, where a region encompassed by the inner ridge defines a primary drainage region into which fluid from the anterior chamber or posterior chamber of the eye can be drained when in use,
c) optionally an outer ridge located on the upper surface of the plate, provided that the height of the inner ridge relative to the surface of the plate is greater than the height of the outer ridge relative to the surface of the plate,
d) a secondary drainage region outside the inner ridge into which fluid from the primary drainage region can be received when in use, where the secondary drainage region is defined by the inner ridge and either the edge of the plate or the outer ridge, and
e) a hole in the inner ridge having a size enabling a drainage tube for draining the fluid from the anterior chamber or posterior chamber of the eye to the primary drainage region to be connected to the hole so that fluid can be transferred through the tube and into the primary drainage region.

In one embodiment of the invention, the implant has an outer ridge. Preferably, the outer ridge is located at or proximal to the edge of the plate. In an alternative embodiment, the implant has no outer ridge.

In a preferred embodiment, the implant includes the drainage tube. Preferably, the plate has suture holes each located near the edge of the plate to allow the implant to be sutured to the surface of the eyeball. Typically, the implant will have four suture holes, although only two of the suture holes would routinely be used.

It is preferred that the surface area of the primary drainage region is up to about one quarter of the surface area of the plate.

It is further preferred that the inner ridge has dimensions suitable to allow overlying Tenon's tissue to exert tension on the inner ridge so that fluid can escape from the drainage region onto the remainder of the surface of the plate only when the fluid pressure reaches a certain level. The pressure is preferably greater than about 12 to 15 mmHg.

The dimensions of the plate are preferably selected so that the plate can be inserted at least partly beneath adjacent rectus muscle tendons close to their insertions on the eye.

The implant may be made from any suitable material or combination of materials, but is preferably made from polypropylene.

In one embodiment of the invention, the implant has a single inner ridge. In an alternative embodiment of the invention, the implant has more than one inner ridge.

In another embodiment of the invention, the implant is linked to one or more additional implants by one or more interconnecting tubes to allow transfer of fluid from one implant to another.

In a second aspect of the invention there is provided a method of treating or alleviating the symptoms of glaucoma using an implant of the first aspect of the invention by:
a) surgically inserting the implant between the sclera and Tenon's tissue of the eye, and
b) inserting the drainage tube through the surface of the eye and into either the anterior chamber or posterior chamber of the eye to allow fluid to drain from the anterior chamber or posterior chamber into the drainage region of the implant.

The method may include the additional step of temporarily occluding the drainage tube using an absorbable ligature to delay drainage of fluid.

Preferably, the implant is also held in place by one or more sutures, typically two sutures.

BRIEF DESCRIPTION OF FIGURES

The invention will be described by way of example only with reference to the drawings in which.

DETAILED DESCRIPTION

Figure 1:
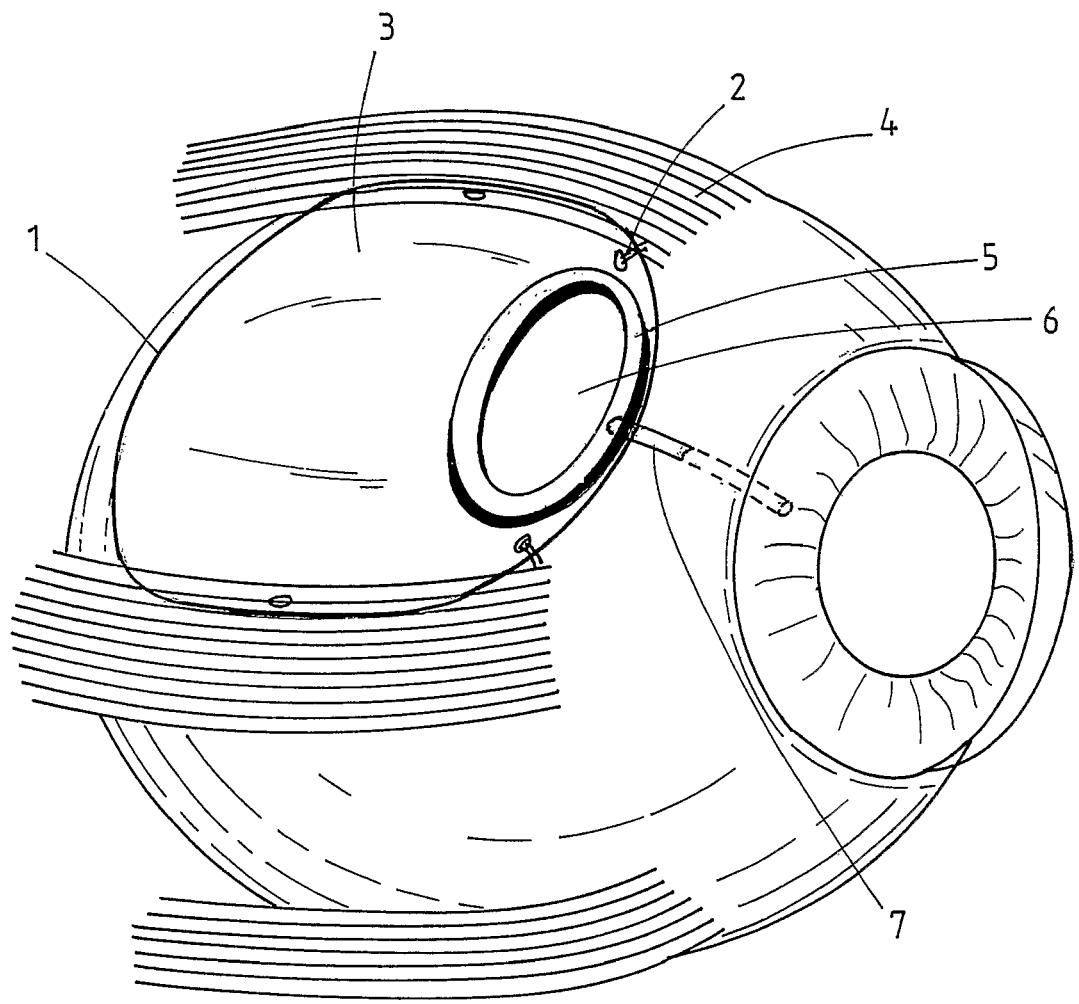
FIG. 1 is a perspective view of an eye with an implant of the invention inserted.

The implant of the invention comprises a plate and tube arrangement of the kind described in U.S. Pat. No. 4,457,757. IOP is reduced by the transfer of aqueous fluid from the interior of the eyeball through the tube to the plate. Fluid that is transferred to the plate is absorbed into surrounding tissues. Preferably, the tube is inserted through the sclera and into the anterior chamber or the posterior chamber of the eye, thus providing fluid communication between the interior of the eye and the surface of the plate.

The present invention also utilises a ridge mechanism as described in U.S. Pat. No. 4,750,901 in order to prevent post-operative hypotony. The ridge mechanism comprises an inner ridge defining a part of the surface area of the plate and an outer ridge at or near to the edge of the plate. However, the ridge mechanism of U.S. Pat. No. 4,750,901 has been improved in this invention by providing an improved connection between the inner ridge and the overlying Tenon's tissue.

The preferred implant of this invention has an enlarged plate relative to some other implants. This provides a greater fluid dispersion area. The need for multiple plate implants is therefore reduced, and the surgical problems associated with multiple plate implants avoided.

The preferred implant of this invention also has either no outer ridge at or near to the edge of the plate, or has a low profile outer ridge. It has been found that an outer ridge is not essential to maintain a bleb over the plate. The reduced outer ridge lowers the profile of the implant making it easier to insert into the Tenon's capsule.

The enlarged plate together with the lower outer ridge of the implant of this invention also helps to improve contact between the inner ridge and the overlying Tenon's tissue. The increased width of the plate allows the implant to be positioned so that at least a portion of each of two opposite sides of the plate lies beneath a rectus muscle insertion. Tenon's tissue that is adjacent to a rectus muscle insertion is reinforced by fibrous expansions which extend from the rectus muscle sheath into Tenon's tissue. This allows Tenon's tissue to be drawn more tightly across the inner ridge during implantation. Consequently, the fluid pressure required to lift Tenon's tissue off the inner ridge to allow fluid to drain from the region encompassed by the inner ridge (the primary drainage region) onto the larger area of the plate beyond the inner ridge (the secondary drainage region) is raised and the ability of the implant to prevent post-operative hypotony is thereby improved.

Enzymes produced by the tissues covering the implant act to remove blood clot or inflammatory exudates that can cause blockage of valve based implants, stud implants, or implants where the drainage tube is located underneath the plate. In addition, any blockage by blood clot or inflammatory exudate that does form is rapidly cleared by enzymes from the overlying tissue. This is not the case with implants with mechanical valves, such as the Krupin and the Ahmed inventions where blockage may require repeated surgery or removal of the implant.

The implant of the invention may be made of any biocompatible material, rigid or flexible. Preferably, the implant is made of polypropylene. In a preferred embodiment, the implant is quite flexible on account of its thinness and the lack of a pronounced outer ridge.

The plate of the implant is curved to fit the curvature of the eyeball. The plate preferably has holes near the edge of the plate which allow sutures to be threaded through the plate for the purpose of attaching the plate to the surface of the eyeball. In a preferred embodiment the plate has four suture holes.

The plate is attached to the surface of the eyeball under the outer tissue layer which is known as Tenon's tissue. At operation, the plate is inserted between the sclera and Tenon's capsule and sutured to the surface of the eyeball (the sclera).

The implant may be positioned in any of the four quadrants of the eye, the superior temporal and superior nasal quadrants being the most commonly used.

Preferably, the plate is positioned so that it lies between the tendon insertions of two adjacent rectus muscles on the surface of the eyeball. The plate is held in place by the normal muscle tone of the adjacent rectus muscles and by sutures which pass through the anterior suture holes of the plate and the tendon insertions of the rectus muscles.

The dimensions of the implant are variable. Preferably however, the width of the plate is such that the sides of the plate can be inserted partly beneath adjacent rectus muscles.

Preferably, the length of the plate is such that it avoids the optic nerve and the blood vessels at the back of the eye. In a preferred embodiment, the plate is designed to fit between and slightly under the edge of each of two adjacent rectus muscles.

The plate of the implant may be linked to one or more other plates with interconnecting tubes to allow passage of fluid from the first (primary) plate to subsidiary plates. However, in a preferred embodiment of the invention, the implant has a plate of sufficient surface area to eliminate the need for multiple plate implants in most cases.

An outer ridge may be present with a low profile or may be absent from the surface of the plate. The applicant has found that a pronounced outer ridge is not necessary for bleb formation and maintenance. In a preferred embodiment, the outer ridge is significantly reduced in size relative to the outer ridge described in U.S. Pat. No. 4,750,901. Reduction or removal of the outer ridge provides an implant having a reduced profile which is therefore easier to insert into Tenon's capsule.

As noted above, a problem associated with implants of this kind is an excessive lowering of IOP following implantation (post-operative hypotony). This can cause damage to the eye resulting in impairment of vision.

This problem is avoided in the present invention by utilising a ridge mechanism as described in U.S. Pat. No. 4,750,901. However, the ridge mechanism of U.S. Pat. No. 4,750,901 has been improved in this invention by providing an improved connection between the inner ridge and the overlying Tenon's tissue.

The inner ridge incorporates the opening of the tube onto the upper surface of the plate.

The size of the region defined by the inner ridge (the primary drainage region) may vary from an area just big enough to incorporate the opening of the tube where it emerges onto the surface of the plate, to an area that occupies a large proportion of the plate. However, the larger the primary drainage region, the lower the pressure at which fluid can escape into the secondary drainage region. In a preferred embodiment, the primary drainage region occupies less than one quarter of the surface area of the plate.

The implant may have additional ridges each of which define a further ridged area at different locations on the surface of the plate. The ridge principle of this invention may also be applied to any subsidiary plate arrangements.

During implantation, Tenon's tissue is drawn forward and stretched to cover the inner ridge of the plate of the implant and sutured firmly to the sclera just in front of the plate. This creates a chamber into which fluid from the anterior chamber or posterior chamber of the eye is drained. The tension that the tissue exerts on the inner ridge enables fluid to escape on to the plate beyond the inner ridge, to the secondary drainage region, only when the pressure reaches a certain level.

When fluid begins to flow through the tube of the implant, Tenon's tissue, stretched over the inner ridge of the implant, provides sufficient resistance to the escape of fluid from the eye to limit drainage of fluid to the primary drainage region. This reduces the possibility of fluid from the eye being too readily absorbed into the Tenon's tissue overlying the larger area of entire plate in the initial few days after surgery and therefore avoids post-operative hypotony. When the IOP rises to a sufficient level to lift Tenon's tissue off the inner ridge, drainage through the entire area of Tenon's tissue overlying the plate of the implant commences and the IOP falls gradually. If the IOP reduces below the above level, the Tenon's tissue will return to contact with the inner ridge to reduce or prevent flow of fluid into the secondary drainage region. In this way, the inner ridge in combination with the Tenon's tissue acts as a valve.

The thickness of Tenon's tissue varies. It is greatest between the equator of the eye and the tendon insertions of the muscles. In a preferred embodiment of the invention, it is this thicker portion of Tenon's tissue that is stretched over the inner ridge of the implant at operation. Manipulation of the tissues at the time of operation, together with the pro-inflammatory effect of the fluid on the tissues, raises the pressure in Tenon's tissue to about 12 to 15 mmHg. Preferably, IOP must be more than about 12 to 15 mmHg before Tenon's tissue is lifted off the inner ridge of the implant to allow drainage of fluid into the secondary drainage region.

An absorbable ligature may or may not be used to delay drainage of fluid in appropriate cases.

The invention will now be further described by way of example only with reference to FIGS. 1 to 4 of the drawings.

FIG. 1 shows the implant 1 of the invention attached to the surface of an eyeball by sutures 2 threaded through holes positioned near the edge of the implant plate 3. The plate 3 is positioned between the tendon insertions of two rectus muscles 4 so that a portion of each of two opposite sides of the plate 3 lies beneath a rectus muscle insertion.

The plate 3 is curved to fit the curvature of the eye and to enable the plate 3 to sit neatly on the surface of the eye.

An oval shaped inner ridge 5 extends from the upper (convex) surface of the plate 3 at the front edge of the plate 3 (in relation to the eye). The inner ridge 5 forms a primary drainage region 6 on the upper surface of the plate 3.

Figure 2:
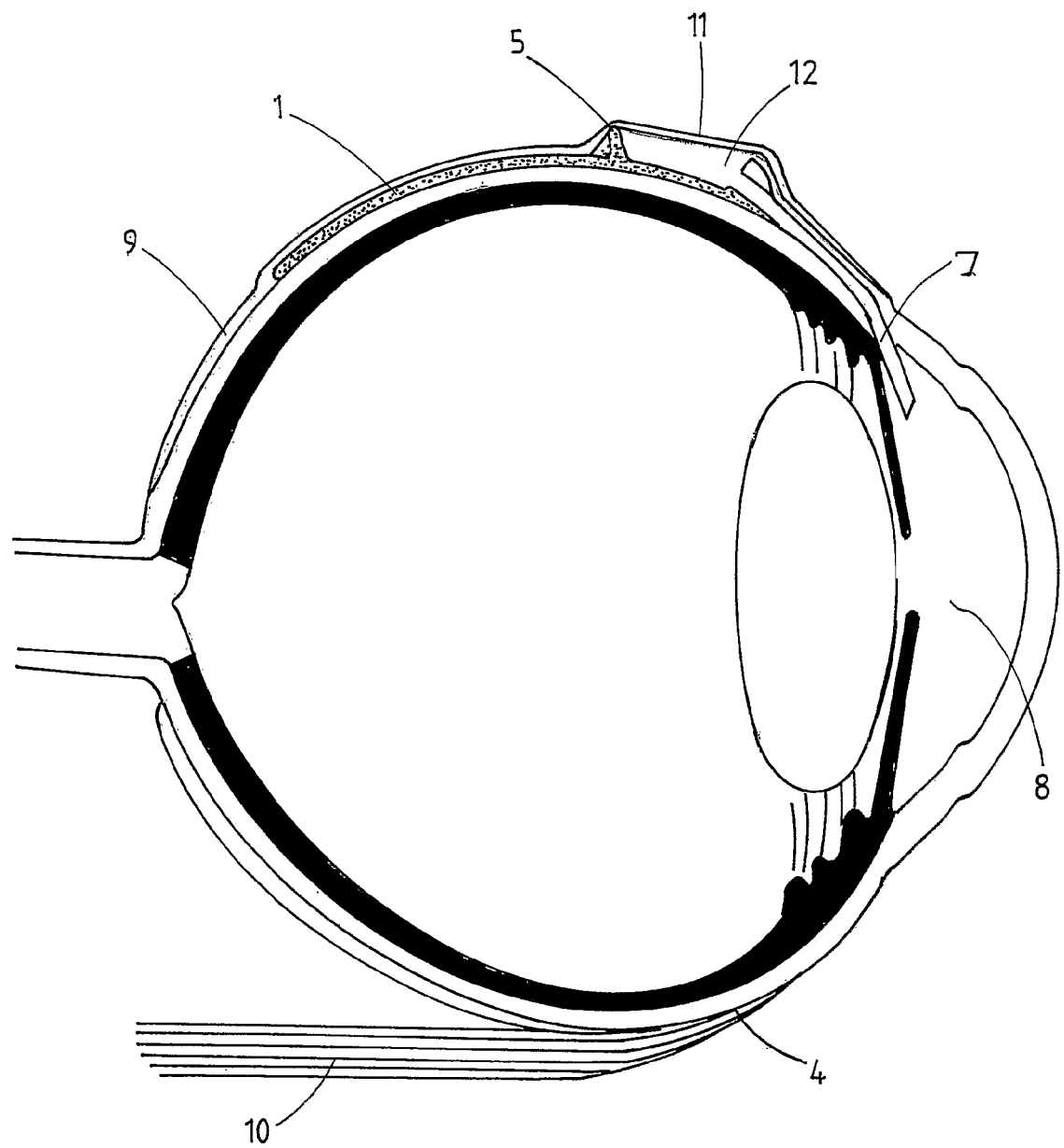
FIG. 2 is a side cross-sectional view of an eye with an implant of the invention inserted.

A translimbal tube 7 extends from the region 6, through the limbal tissue, into the anterior chamber 8 of the eye, as shown in FIG. 2. The translimbal tube 7 enables the transfer of fluid from the anterior chamber 8 of the eye into the region 6, thereby reducing pressure within the anterior chamber 8.

As shown in FIG. 2, the implant 1 is located on the upper surface of the eye beneath the outer tissue layer of the eyeball (Tenon's capsule 9). The rectus muscle 10 is in contact with the eyeball from the equator of the eyeball to the point at which the rectus muscle 10 is anchored to the anterior surface of the eyeball (the rectus muscle tendon insertion 4). Posterior Tenon's tissue is relatively thin. However, anterior Tenon's tissue is thicker due to reinforcement by fibrous expansions that extend from the rectus muscle sheaths. This reinforced thicker anterior portion of Tenon's tissue 11 covers the region 6 and is held in contact with the inner ridge 5 and stretched over it by the natural muscle tone of the adjacent rectus muscles 4. This helps to maintain contact between the inner ridge 5 and the overlying tissue 11.

FIG. 2 further shows that Tenon's tissue forms a layer over the region 6 on the upper surface of the plate 3, thereby defining a chamber 12. The chamber 12 is capable of holding fluid transferred from the anterior chamber 8 of the eye through the tube 7.

Figure 3:
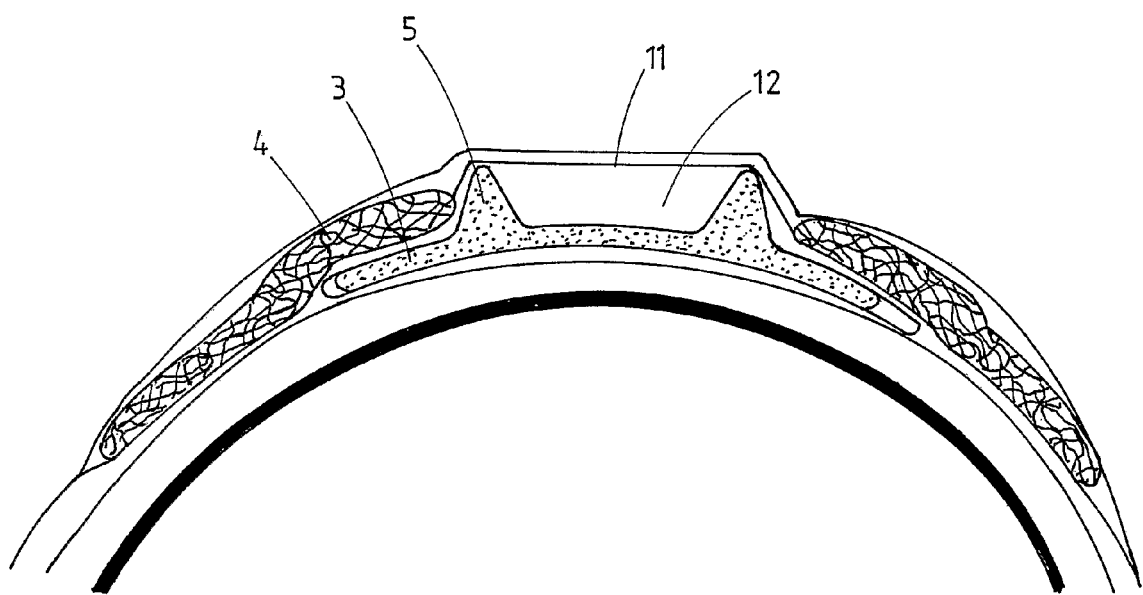
FIG. 3 is a front cross-sectional view through part of the wall of an eyeball in which the implant of the invention has been inserted.

The chamber 12 is further illustrated in FIG. 3. FIG. 3 also illustrates the sides of the plate 3 immediately behind a rectus muscle insertion 4 and the Tenon's tissue that forms a layer over the inner ridge 5 thickened by fibrous expansions from the rectus muscle sheaths and held in contact with the inner ridge 5 by the tone of the muscles.

Figure 4:
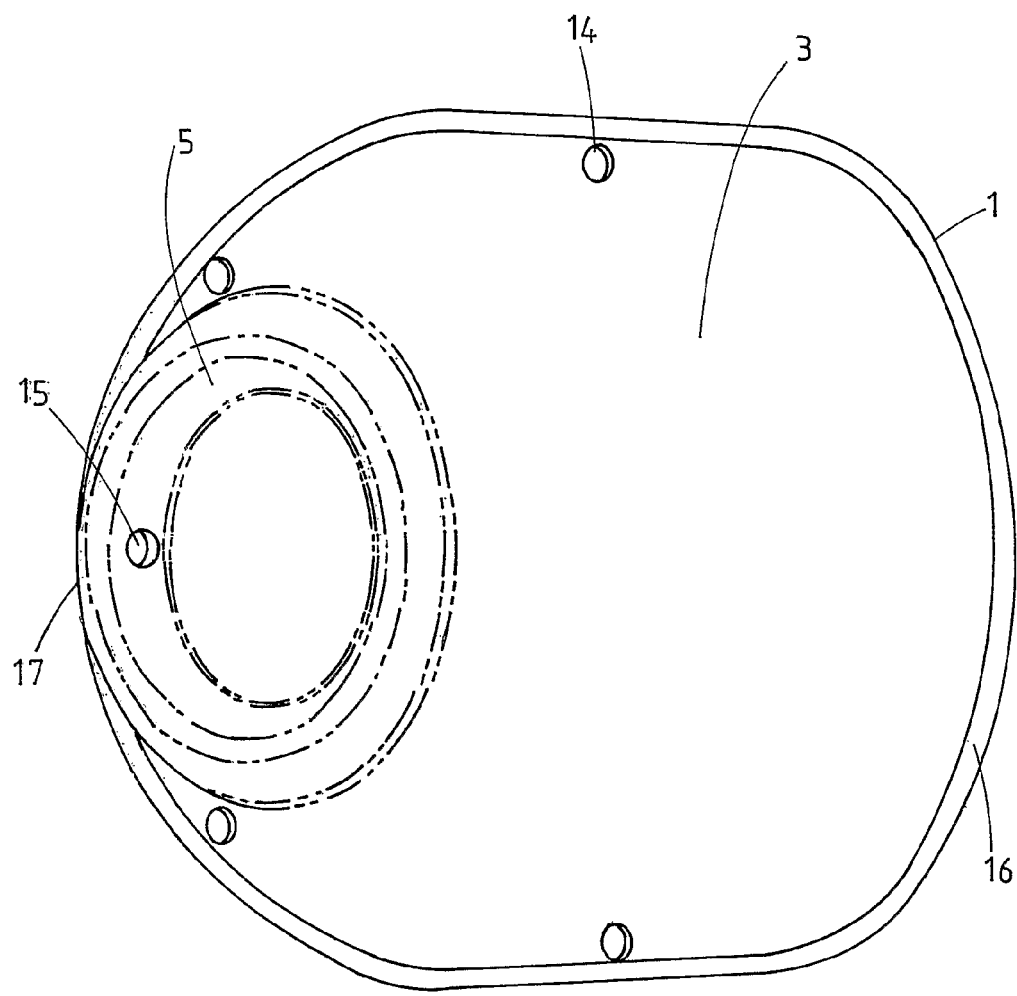
FIG. 4 is a perspective view of the implant of the invention.

FIG. 4 shows that the plate 3 has a rounded shape with curved front and rear ends but straighter sides, and also possesses four holes 14 located near the edge of the plate 3. The holes 14 allow the plate 3 to be sutured to the surface of an eyeball.

The inner ridge 5 extends from the surface of the plate 3 near the front end 17 of the plate 3. The portion of the inner ridge 5 closest to the periphery of the plate 3 has a hole 15. The end of a translimbal tube (not shown in FIG. 4) fits snugly into the hole 15 from the exterior of the inner ridge 5 and leads to the anterior chamber of the eye when the implant 1 is surgically implanted. An outer ridge 16 is located at the edge of the plate 3 and merges with the ridge 5 at the front end 17 of the plate 3.

The invention therefore provides an implant based on the tube and plate design of NZ 215409 which provides a greater fluid dispersion area within a single plate and tube device, a lower profile for easier implantation, and improved contact between the inner ridge and the overlying Tenon's tissue. The implant of the invention therefore improves the ability of the implant to prevent post-operative hypotony. The plate, together with the living tissue covering it, form a biological tissue/plate valve which regulates the escape of fluid from the eye in the early postoperative period. Unlike valve based implants, stud implants, or implants wherein the drainage tube is located underneath the plate which can become blocked by blood clot or inflammatory exudates, this biological valve system ensures that the drainage system cannot become blocked by blood clot or inflammatory exudates.

Although the invention has been described by way of example, it should be appreciated that variations and modifications may be made without departing from the scope of the claims. Furthermore, where known equivalents exist to specific features, such equivalents are incorporated as if specifically referred in this specification.

INDUSTRIAL APPLICABILITY

The ophthalmic implant of the invention is useful for treating or alleviating the symptoms of glaucoma. Following surgical implantation, the implant (with drainage tube attached) enables fluid to be transferred from within the eye to the upper surface of the implant's plate and from there the fluid is absorbed into surrounding tissue. Intraocular pressure is thereby reduced and the effects of glaucoma alleviated.

The invention claimed is:

1. An ophthalmic implant for treating or alleviating the symptoms of glaucoma, the implant having:
   (a) a plate shaped to fit the surface of an eye when implanted,
   (b) an inner ridge located on the upper surface of the plate, where a region encompassed by the inner ridge defines a primary drainage region into which fluid from the anterior chamber or posterior chamber of the eye can be drained when in use,
   (c) a boundary structure located on the upper surface of the plate outward of the inner ridge, provided that the height of the inner ridge relative to the surface of the plate is greater than the height of the boundary structure relative to the surface of the plate,
   (d) a secondary drainage region outside the inner ridge into which fluid from the primary drainage region can be received when in use, where the secondary drainage region is defined by the inner ridge and the boundary structure, and
   (e) a hole in the inner ridge having a size enabling a drainage tube for draining the fluid from the anterior chamber or posterior chamber of the eye to the primary drainage region to be connected to the hole so that fluid can be transferred through the tube and into the primary drainage region.

2. The ophthalmic implant of claim 1 wherein the boundary structure comprises an outer ridge.

3. The ophthalmic implant of claim 2 where the outer ridge is located at or proximal to the edge of the plate.

4. The ophthalmic implant of claim 1 wherein the boundary structure has a height of zero and corresponds to the edge of the plate.

5. The ophthalmic implant of claim 1 including the drainage tube.

6. The ophthalmic implant of claim 1 where the plate has at least two suture holes, each suture hole located near the edge of the plate to allow the implant to be sutured to the surface of the eyeball.

7. The ophthalmic implant of claim 6 where the plate has two suture holes.

8. The ophthalmic implant of claim 6 where the plate has four suture holes.

9. The ophthalmic implant of claim 1 where the surface area of the primary drainage region is up to about one quarter of the surface area of the plate.

10. The ophthalmic implant of claim 1 where the inner ridge has dimensions suitable to allow overlying Tenon's tissue to exert tension on the inner ridge so that fluid can escape from the drainage region onto the remainder of the surface of the plate only when the fluid pressure reaches a certain level.

11. The ophthalmic implant of claim 10 where the fluid pressure is greater than about 12 to 15 mmHg.

12. The ophthalmic implant of claim 1 where the dimensions of the plate enable the plate to be inserted at least partly beneath adjacent rectus muscle tendons close to their insertions on the eye.

13. The ophthalmic implant of claim 1 where the implant is made from polypropylene.

14. The ophthalmic implant of claim 1 where the implant has more than one inner ridge.

15. The ophthalmic implant of claim 1 where the implant is linked to one or more additional implants by one or more interconnecting tubes to allow transfer of fluid from one implant to another.

16. A method of treating or alleviating the symptoms of glaucoma using an implant of claim 1 by:
   (a) surgically inserting the implant between the sclera and Tenon's tissue of the eye, and
   (b) inserting the drainage tube through the surface of the eye and into either the anterior chamber or posterior chamber of the eye to allow fluid to drain from the anterior chamber into the drainage region of the implant.

17. The method of claim 16 further including the step of temporarily occluding the drainage tube using an absorbable ligature to delay drainage of fluid.

18. The method of claim 16 where the implant is held in place by one or more sutures.

19. The method of claim 18 where the implant is held in place by two sutures.

* * * * *